United States Patent
Farina et al.

(10) Patent No.: US 7,732,473 B2
(45) Date of Patent: Jun. 8, 2010

(54) COMPOUNDS WITH NOOTROPIC ACTION, THEIR PREPARATION, PHARMACEUTICAL COMPOSITIONS CONTAINING THEM, AND USE THEREOF

(75) Inventors: Carlo Farina, Milan (IT); Stefania Gagliardi, Vimercate (IT); Carlo Parini, Magenta (IT); Marisa Martinelli, Villa Guardia (IT); Carla Ghelardini, Florence (IT)

(73) Assignee: Neurotune AG, Schlieren-Zurich (CH)

( * ) Notice: Subject to any disclaimer, the term of this patent is extended or adjusted under 35 U.S.C. 154(b) by 0 days.

(21) Appl. No.: 12/378,475

(22) Filed: Feb. 13, 2009

(65) Prior Publication Data

US 2009/0163565 A1 Jun. 25, 2009

Related U.S. Application Data

(62) Division of application No. 10/550,483, filed on Jun. 16, 2006, now Pat. No. 7,544,705.

(51) Int. Cl.
*A61K 31/4166* (2006.01)
*C07D 235/00* (2006.01)

(52) U.S. Cl. .................. 514/387; 548/301.7; 548/302.7; 514/385

(58) Field of Classification Search ............. 548/301.7, 548/302.7; 514/385, 387
See application file for complete search history.

(56) References Cited

U.S. PATENT DOCUMENTS

| 5,130,319 A * | 7/1992 | Pinza et al. .................. 514/300 |
| 5,200,406 A * | 4/1993 | Pinza et al. ............ 514/212.05 |
| 7,544,705 B2 * | 6/2009 | Farina et al. ................. 514/387 |

* cited by examiner

*Primary Examiner*—Golam M Shameem
(74) *Attorney, Agent, or Firm*—Abelman, Frayne & Schwab

(57) ABSTRACT

Described herein are new bicyclic arylimidazolones having nootropic action (i.e., protecting and stimulating cerebral functions), analgesic action and anti hyperalgesic action; also described is the process for their preparation and pharmaceutical compositions comprising them, useful for the treatment of cognitive deficits, and of various types of pain.

8 Claims, 2 Drawing Sheets

COMPOUNDS WITH NOOTROPIC ACTION, THEIR PREPARATION, PHARMACEUTICAL COMPOSITIONS CONTAINING THEM, AND USE THEREOF

The subject application is a division of U.S. application Ser. No. 10/550,483, filed Jun. 16, 2006, now U.S. Pat. No. 7,544,705.

FIELD OF THE INVENTION

The present Invention relates to new compounds of formula (I) appearing hereinafter, their process of preparation, the pharmaceutical compositions containing them, and their use as nootropic, neuroprotective, analgesic and anti-hyperalgesic agents.

STATE OF THE ART

Compounds that possess nootropic activity are already known in the literature. In particular, the derivatives substituted in position 4 of 2-oxo-1-pyrrolidineacetamide are valid psychotropic agents that re-establish damaged cognitive functions. These compounds are described, for example, in *Pharm. Res. Commun.* 16, 67, 1984 by Banfi et al. and in *Drug Development Res.* 2, 447, 1982 by Itil et al.

Amongst the most widely known molecules belonging to the class mentioned above there may be cited: 2-oxo-1-pyrrolidineacetamide (piracetam), 4-hydroxy-2-oxo-1-pyrrolidineacetamide (oxiracetam), 2-(2-oxopyrrolidin-1-yl) butyramide (levetiracetam) and N-2,5-dimethylphenyl)-2-oxo-1-pyrrolidineacetamide (nefiracetam).

Another chemical class that possesses nootropic activity is represented by imidazolic condensed derivatives, in particular 2,5-dioxohexahydro-1H-pyrrolo[1,2-a]imidazole (dimiracetam), described in EP 335483 and in WO-9309120, and in *J. Med. Chem.*, 36,4214, 1993 by Pinza M. et al.

Recently, it has been demonstrated that nefiracetam could be a good therapeutic agent in the treatment of neuropathic pain. The anti-hyperalgesic action induced by nefiracetam appears to be of non-opioid nature and is probably due to the stimulation of the nicotinic cholinergic system at a spinal and superspinal level (Rashid Harunor M.D. *J. Pharmacol. Exp. Ther*, 303, 226, 2002).

SUMMARY OF THE INVENTION

The present applicant has now found new N-substituted bicyclic imidazolones of formula (I), appearing hereinafter, that have demonstrated improved psychotropic properties and more marked analgesic and antihyperalgesic effects in numerous models of neuropathic pain, with respect to the already known nootropic agents.

The present compounds of formula (I) are consequently useful in the treatment of many disorders of the central nervous system (CNS), for example in the deterioration of learning, dysfunctions of the cognitive sphere and of the memory, Alzheimer's disease, dementias, including senile dementia of the Alzheimer type, post stroke vascular type dementia, epilepsy, cerebral ischaemia, mood disorders, including depression, chronic, inflammatory, neuropathic and visceral pain, and emesis.

Consequently, representative of the subject of the present invention are compounds of the general formula (I)

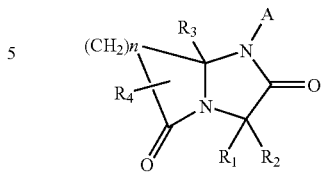

in which:
A is chosen among carbocylic aromatic groups, heterocyclic aromatic groups and arylC$_{1-4}$alkyl;
R$_1$ is chosen among:
hydrogen,
arylC$_{1-7}$alkyl, optionally substituted on the aryl moiety with one or more groups chosen among hydroxy, C$_{1-4}$alkoxy, halogen, haloC$_{1-4}$alkyl;
heterocyclylC$_{1-7}$alkyl, optionally substituted on the heterocyclyl moiety with one or more groups chosen among C$_{1-4}$alkyl and hydroxy;
C$_{1-7}$ alkyl, optionally Interrupted by an oxygen or sulphur atom or optionally substituted at any position by one or more groups chosen among hydroxy, thio, amino, carboxyl, aminocarbonyl, guanidinyl.
R$_2$ is chosen among hydrogen, C$_{1-4}$alkyl, arylC$_{1-4}$alkyl and phenyl; or else R$_1$ and R$_2$, taken together, form a saturated carbocyclic ring containing from 3 to 8 carbon atoms;
R$_3$ is chosen among hydrogen, C$_{1-4}$alkyl, arylC$_{1-4}$alkyl, CONH$_2$ and COOR$_5$ in which R$_5$ is chosen between hydrogen and C$_{1-4}$alkyl;
R$_4$ is chosen among hydrogen, C$_{1-4}$alkyl, aryl, arylC$_{1-4}$alkyl and heterocyclyl; and
n is 2, 3 or 4;

in the form of a racemic mixture or in the form of enantiomers, and pharmaceutically acceptable salts or solvates thereof.

The process of preparation of the compounds of formula (I) appearing above, the pharmaceutical compositions containing them and their use for the preparation of medicaments with nootropic and neuroprotective action, with analgesic and/or anti-hyperalgesic action, and anti-emetic action, constitute a further subject of the invention.

Characteristics and advantages of the present compounds of formula (I) will be illustrated in detail in the following description.

DETAILED DESCRIPTION OF THE INVENTION

Figure 1A:
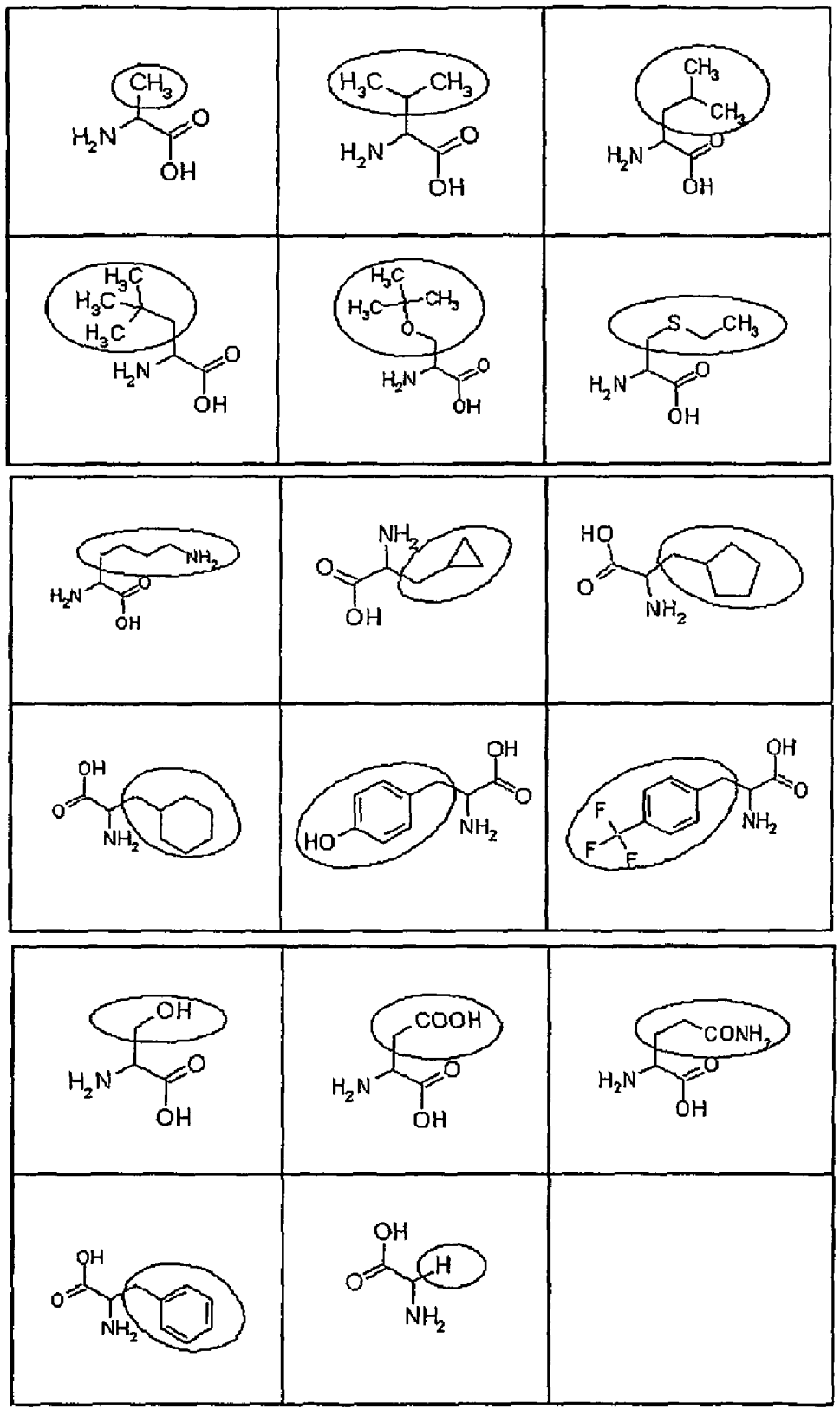
FIGS. 1a, 1b: non limiting examples of aminoacids of formula (IV), useful in the synthesis of the compounds of formula (I). The encircled portion indicates the substituent R$_1$.

In the framework of the present invention, the term "carbocyclic aromatic group" means single or fused aromatic rings with 6 to 12 ring members, optionally substituted.

The terms "heterocyclic aromatic group" and "heterocyclyl" mean single or fused aromatic rings, each ring having 5 to 12 members and comprising up to four hetero atoms, chosen among oxygen, sulphur and nitrogen, optionally substituted.

Whenever not otherwise specified, the term "aryl" means single or fused unsaturated rings, each ring having from 5 to 8 members, and preferably 5 or 6 members, optionally substituted; by the term "arylC$_{1-4}$alkyl" is indicated a group having an aryl group, as defined above, and a C$_{1-4}$ alkyl moiety connecting the aryl group to the point of substitution.

All the aforesaid C$_{1-4}$ alkyl groups, including those being part of the arylC$_{1-4}$alkyl group, may be indifferently linear or branched or cyclic (i.e cyclopropyl, cyclopropylmethyl or methylcyclopropyl). Preferred C1-C4 alkyl groups are Me, Et, I—Pr, I—Bu, and cyclopropylmethyl.

All the aforesaid C$_{1-7}$ alkyl groups, including those being part of C$_{1-7}$ alkyl-containing groups, can either be linear, branched or cyclic, and may include double or triple bonds. The term "C$_{1-7}$ alkyl groups interrupted by oxygen or sulphur" means, respectively, any ether and thioether groups containing from 1 to 7 carbon atoms.

By the term "heterocyclylC$_{1-7}$alkyl" is indicated a group having an heterocyclyl group, as defined above, and a C$_{1-7}$ alkyl moiety connecting the aryl group to the point of substitution.

By the term "arylC$_{1-7}$alkyl" is indicated a group having an aryl group, as defined above, and a C$_{1-7}$ alkyl moiety connecting the aryl group to the point of substitution.

By "halogen" is meant an atom chosen among fluorine, chlorine, bromine or iodine; by "haloC$_{1-4}$alkyl" is meant a C$_{1-4}$ alkyl group substituted at any position by one or more halogen atoms, e.g. trifluoromethyl.

Unless differently specified, "optionally substituted" groups are groups optionally substituted with 1 to 3 substituents, chosen preferably among Me, Et, I—Pr, OH, COOEt, COOH, CH$_2$OH, SO$_2$NH$_2$, SO$_2$Me, OMe, Cl, F, CN and CF$_3$, and more preferably among Me, Et, I—Pr, OH, CN, C$_1$ and CF$_3$; the substituents may be in any position of the group to be substituted.

Preferred compounds according to the invention are the compounds of formula (I), in which A is a optionally substituted phenyl, optionally substituted benzyl, or else a optionally substituted heterocyclic aromatic group with 5 or 6 members and comprising up to two hetero atoms chosen between oxygen, sulphur and nitrogen, R$_1$, R$_2$, R$_3$ and R$_4$ are chosen among hydrogen, C$_{1-4}$ alkyl or benzyl, and n is equal to 2 or 3.

Preferably, A is phenyl, thienyl, pyridyl, pyrimidinyl group, optionally substituted, benzyl or 4-methylbenzyl; R$_1$ is hydrogen, C$_{1-4}$ alkyl (for example methyl, isopropyl or isobutyl), benzyl, —CH$_2$OH, —CH$_2$CH$_2$CONH$_2$, —CH$_2$COOH, indol(3-yl)methyl, R$_2$ is hydrogen, C$_{1-4}$ alkyl or benzyl, R$_3$ and R$_4$ are hydrogen or methyl, and n is 2.

More preferably, A is a phenyl, optionally substituted, R$_1$, R$_2$, R$_3$ and R$_4$ are hydrogen, and n is equal to 2.

When R$_1$ and R$_2$, taken together, form a saturated carbocyclic ring containing from 3 to 8 carbon atoms, the resulting compound of formula (I) is a spirocyclic compound.

Preferred compounds of formula (I) according to the invention are chosen in the group consisting of:
1-Phenyl-tetrahydro-1H-pyrrolo[1,2a]imidazole-2,5-dione;
1-o-tolyl-tetrahydro-1H-pyrrolo[1,2-a]imidazole-2,5-dione;
1-(2,6-Dimethyl-phenyl)-tetrahydro-pyrrolo[1,2-a]imidazole-2,5-dione;
1-Thiophen-2-yl-tetrahydro-pyrrolo[1,2-a]imidazole-2,5-dione;
1-m-Tolyl-tetrahydro-pyrrolo[1,2-a]imidazole-2,5-dione;
1-p-Tolyl-tetrahydro-pyrrolo[1,2-a]imidazole-2,5-dione;
1-(5-Fluoro-2-methyl-phenyl)-tetrahydro-pyrrolo[1,2-a]imidazole-2,5-dione;
1-(3-Fluoro-2-methyl-phenyl)tetrahydro-pyrrolo[1,2-a]imidazole-2,5-dione;
1-(2-Trifluoromethyl-phenyl)-tetrahydro-pyrrolo[1,2-a]imidazole-2,5-dione;
1-(4-Chloro-2-methyl-phenyl)-tetrahydro-pyrrolo[1,2-a]imidazole-2,5-dione;
1-(3-Chloro-phenyl)-tetrahydro-pyrrolo[1,2-a]imidazole-2,5-dione;
1-(3-Methoxy-phenyl)-tetrahydro-pyrrolo[1,2-a]imidazole-2,5-dione;
1-(3-Cyano-phenyl)-tetrahydro-pyrrolo[1,2-a]imidazole-2,5-dione;
1-(4-Chloro-phenyl)-tetrahydro-pyrrolo[1,2-a]imidazole-2,5-dione;
1-(3-Hydroxy-phenyl)-tetrahydro-pyrrolo[1,2-a]imidazole-2,5-dione;
1-(3-Trifluoromethyl-phenyl)-tetrahydro-pyrrolo[1,2-a]imidazole-2,5-dione;
1-(4-Trifluoromethyl-phenyl)-tetrahydro-pyrrolo[1,2-a]imidazole-2,5-dione;
1-(4-Methoxy-phenyl)-tetrahydro-pyrrolo[1,2-a]imidazole-2,5-dione;
1-(3,5-Dimethyl-phenyl)-tetrahydro-pyrrolo[1,2-a]imidazole-2,5-dione;
1-(3,4-Dimethyl-phenyl)-tetrahydro-pyrrolo[1,2-a]imidazole-2,5-dione;
1-Naphthalen-2-yl-tetrahydro-pyrrolo[1,2-a]imidazole-2,5-dione;
1-(3-Isopropyl-phenyl)-tetrahydro-pyrrolo[1,2-a]imidazole-2,5-dione;
1-(4-Chloro-3-methyl-phenyl)-tetrahydro-pyrrolo[1,2-a]imidazole-2,5-dione;
3-Benzyl-1-phenyl-tetrahydro-pyrrolo[1,2-a]imidazole-2,5-dione;
3-Methyl-1-phenyl-tetrahydro-pyrrolo[1,2-a]imidazole-2,5-dione;
3-Isobutyl-1-phenyl-tetrahydro-pyrrolo[1,2-a]imidazole-2,5-dione;
1-(3-Fluoro-5-methyl-phenyl)-tetrahydro-pyrrolo[1,2-a]imidazole-2,5-dione;
1-(3-Fluoro-4-methyl-phenyl)-tetrahydro-pyrrolo[1,2-a]imidazole-2,5-dione;
7a-Methyl-1-phenyl-tetrahydro-pyrrolo[1,2-a]imidazole-2,5-dione;
(S)-1-o-Tolyl-tetrahydro-pyrrolo[1,2-a]imidazole-2,5-dione;
(R)-1-o-Tolyl-tetrahydro-pyrrolo[1,2-a]imidazole-2,5-dione;
1-(4-Ethyl-phenyl)-tetrahydro-pyrrolo[1,2-a]imidazole-2,5-dione;
1-(4-Isopropyl-phenyl)-tetrahydro-pyrrolo[1,2-a]imidazole-2,5-dione;
1-(4-Hydroxymethyl-phenyl)-tetrahydro-pyrrolo[1,2-a]imidazole-2,5-dione;
4-(2,5-Dioxo-hexahydro-pyrrolo[1,2-a]imidazol-1-yl)-benzoic acid;
4-(2,5-Dioxo-hexahydro-pyrrolo[1,2-a]imidazol-1-yl)-benzoic acid ethyl ester;
1-(4-Methanesulfonyl-phenyl)-tetrahydro-pyrrolo[1,2-a]imidazole-2,5-dione;
1-(4-Fluoro-phenyl)-tetrahydro-pyrrolo[1,2-a]imidazole-,5-dione;
1-(4-Cyano-phenyl)-tetrahydro-pyrrolo[1,2-a]imidazole-2,5-dione;
1-Pyridin-2-yl-tetrahydro-pyrrolo[1,2-a]imidazole-2,5-dione;

1-Pyridin-3-yl-tetrahydro-pyrrolo[1,2-a]imidazole-2,5-dione;
1-(5-Methylpyridin-2-yl)-tetrahydropyrrolo[1,2-a]imidazole-2,5-dione;
1-(2-Cyano-phenyl)-tetrahydro-pyrrolo[1,2-a]imidazole-2,5-dione;
1-(3-Fluoro-phenyl)-tetrahydro-pyrrolo[1,2-a]imidazole-2,5-dione;
1-Benzyl-tetrahydro-pyrrolo[1,2-a]imidazole-2,5-dione;
1-(4-methylbenzyl)-tetrahydro-pyrrolo[1,2-a]imidazole-2,5-dione.

It will be noted that some compounds of formula (I) can contain one or more stereogenic centres. The present invention extends to all the optical isomers of these compounds in their forms entirely or partially resolved and In the form of racemic mixtures.

A further subject of the invention is a process for the preparation of the compounds of formula (I), or one of their salts, and/or one of their solvates, comprising the reaction of a compound of formula (II)

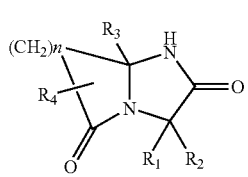
(II)

with a compound of formula (III)

A-X    (III)

in which A, $R_1$, $R_2$, $R_3$, $R_4$ and n are defined as above for the compounds of formula (I), and X is a halogen atom, chosen preferably between bromine and iodine.

When A is a aromatic carbocyclic group or a heterocyclic aromatic group as above defined, the reaction between the compounds of formula (II) and the compound of formula (III) can be conducted according to the appropriate conditions of the Goldberg reaction (*Angew. Chem. Int. E.*, 39, 4492, 2000). In particular, the compounds of formula (II) are dissolved in a suitable solvent, such as N-methylpyrrolidone, together with the compounds of formula (III) in the presence of a catalytic amount of copper salt such as copper iodide, and a base such as potassium carbonate, at any temperature that will yield an adequate percentage of formation of the product required, suitably at a high temperature, such as a temperature of between 60° C. and 140° C., for example at 120° C. The reaction mixture is heated using a system of conventional heating or a microwave reactor of adequate power, for example comprised between 25 and 250 W (*Tetrahedron Letters*, 43, 1101, 2002).

When A is aryl$C_{1-4}$alkyl, the reaction can be carried out in a suitable solvent such as acetonitrile, methylene chloride, acetone, in the presence of a suitable base such as triethylamine, potassium carbonate, 2-tert-Butylimino-2-diethylamino-1,3-dimethylperhydro-1,3,2-diazaphosphorine (also known as BEMP), N,N-Diisopropylethylamine (also known as Hunig base), at a suitable temperature such as reflux temperature (60-140° C., preferably 100° C.).

The aforesaid compounds of formula (II) and the methods for their preparation are described in the European patent application EP-A-335483 and in the International patent application No. WO-A-93/09120 and in *J. Med. Chem.*, 36, 4214, 1993, by Pinza et al.

The compounds of formula (III) are commercially available or can be prepared from known compounds by known methods.

Alternatively, the compounds of formula (I) can be prepared with a process comprising the following stages:

i) reaction of an aminoacid of formula (IV) or of one of its activated derivatives

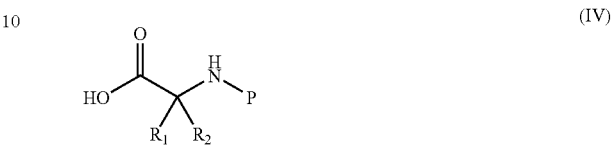
(IV)

with a compound of formula (V)

A-NH$_2$    (V)

to obtain a compound of formula (VI)

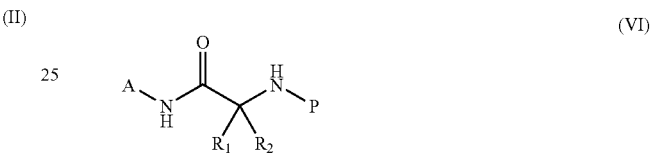
(VI)

in which $R_1$, $R_2$ and A are as defined above for the compound of formula (I), and P is H or a suitable protective group. The activation of aminoacids is a well-known synthetic procedure; examples of activated derivatives of the aminoacids are mixed anhydrides, acyl chlorides and activated esters.

ii) reaction of the compound of formula (VI) obtained at stage i) with a compound of formula (VII)

(VII)

to obtain a compound of formula (VIII)

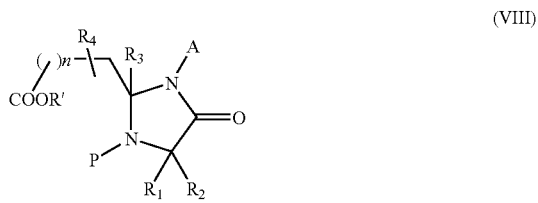
(VIII)

in which A, $R_1$ $R_2$, $R_3$, $R_4$ and n are as defined above for the compound of formula (I), P is defined as above, and R' is an alkyl group;

iii) possible removal of the protective group P by means of hydrogenolysis of the compound of formula (VIII), obtained in stage ii), to obtain the corresponding compound (VIII), in which P is H; and iv) cyclization of the compound of formula (VIII), in which P is H coming from stage ii) or from stage iii), to obtain the desired compound of formula (I).

According to a preferred embodiment of the invention, the alkyl residue R' is chosen between methyl and tert-butyl, and P is chosen between hydrogen, a benzyl or a benzyloxycarbonyl group.

The reaction in stage i) between the compound of formula (IV) and the compound of formula (V) can be performed:

(a) by preparing, in the first place, an acidic chloride of the compound of formula (IV) and uniting to said acidic chloride the compound of formula (V) in the presence of an Inorganic or organic base in an adequate aprotic solvent, such as dimethylformamide (DMF) at a temperature of between −70° C. and 50° C., and preferably between −10° C. and 20° C.; or else:

(b) by reacting together the compound of formula (IV) with the compound of formula (V) in the presence of a suitable condensating agent, such as N,N'-carbonyl diimidazole (CDI) or a carbodiimmide such as dicyclohexylcarbodiimmide (DCC) or N-dimethylaminopropyl-N'-ethylcarbodiimmide, preferably in the presence of N-hydroxybenzotriazole (HOBT) to maximize the yield and prevent the processes of racemization (cf. *Synthesis,* 453, 1972), or O-benzotriazol-1-yl-N,N,N',N'-tetramethyluronium hexafluorophosphate (HBTU), in an aprotic solvent, such as a mixture of acetonitrile (MeCN) and tetrahydrofuran (THF), for example, a mixture with volumetric ratio comprised between 1:9 and 7:3 (MeCN:THF), at any temperature capable of yielding an adequate percentage of formation of the product required, such as a temperature of between −70° C. and 50° C., and preferably between −10° C. and 25° C.

At stage ii) of the present process, the compounds of formula (VI) and (VII) are preferably reflux-heated in a protic solvent, such as water or methanol, and possibly in the presence of a base, such as NaOH, in the case where the compound of formula (VI) is used in the form of one of its salts obtained by addition of acid, for an adequate period of time, preferably comprised between 2 and 24 hours.

Removal of the protective group P by means of hydrogenolysis at stage iii) is preferably conducted using ammonium formulate as a source of hydrogen in a suitable protic solvent, such as methanol or a methanol-water mixture.

The cyclization reaction in stage iv) is carried out directly on the compound of formula (VIII) coming from stage ii) if P is H, or else, if in said compound (VIII) P is a protective group, the first step is to remove it, as described above in stage iii).

The cyclization reaction is conducted in drastic conditions by conventionally heating the compound of formula (VIII) without solvent at 120° C. and in vacuum conditions, or else by means of reflux-heating in xylene for a suitable period of time, for example between 4 hours and 3 days, or by microwave irradiation.

Figure 1B:
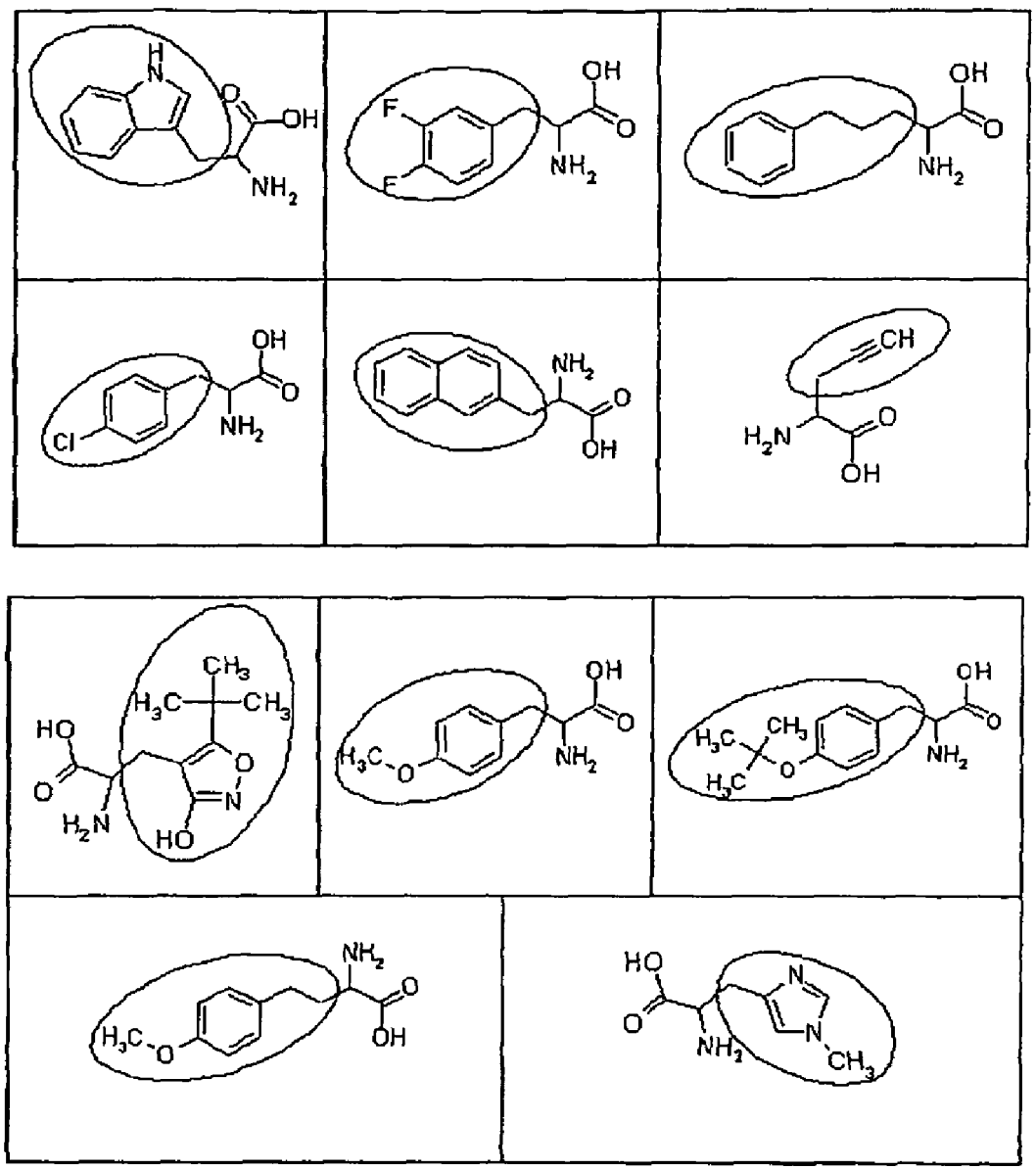

The compounds of formula (IV), (V) and (VII) are commercially available compounds or can be prepared from known compounds using known methods. In particular, the compounds of formula (IV) can be conveniently selected from any naturally occurring aminoacids or derivatives thereof. Examples of aminoacids useful in the present invention are shown in FIG. 1, where the part encircled corresponds to the substituent $R_1$ of formula (IV): accordingly, all these meanings for $R_1$ are also preferred in formula (I), being the object of the present invention.

The present compounds of formula (I) are useful as therapeutic agents and in particular possess a nootropic and neuroprotective activity, i.e., they contribute to restoring the learning and memory functions deteriorated in the process of ageing or on account of ischaemic traumas, and are effective in various pathologies of the CNS, amongst which learning dysfunctions, dysfunctions of the cognitive sphere and of the memory, Alzheimer's disease, dementias, including senile dementia of the Alzheimer type, post stroke vascular type dementia, epilepsy, cerebral ischaemia, and mood disorders, including depression.

The present compounds of formula (I) moreover possess analgesic and/or anti-hyperalgesic activity, i.e., they contribute to combat the sensations of pain, in particular those caused by conditions of neuropathic pain, chronic inflammatory pain and visceral pain, and have proven their efficacy also in the treatment of emesis.

The subject of the present invention is hence also the use of the present compounds of formula (I) or of their pharmaceutically acceptable salts and/or solvates for the preparation of medicaments for recovery of difficulties of learning and memory and for treatment of dementias, Alzheimer's disease, post stroke vascular type dementia, epilepsy, cerebral ischaemia, and mood disorders, including depression.

Also provided is a method to treat the aforesaid diseases and disorders characterised by administering a pharmaceutically active amount of a compound of formula (I) to a patient in need thereof.

It is widely known that cognitive disorders that occur in said pathologies are correlated to the deficit of the cerebral cholinergic system, as emerges from morphological findings (B. E. Tomlinson in "Biochemistry of Dementias"; P. J. Roberts Ed.; John Wiley & Sons, Mew York, N.Y. pp. 15-22, 1980) and neurochemical findings (R. T. Bartus et al. *Science,* 217, 408, 1982). It is moreover well known that the significant deteriorations of cognitive functions are the most evident and debilitating signs observed in patients suffering from Alzheimer's disease, senile dementias of the Alzheimer type, and dementia due to multiple infarcts.

The activity of the compounds of formula (I) can be determined in rats in regard to the amnesia-provoking action of scopolamine (D. A. Drachman, *Archs. Neurol., Chicago,* 30, 113, 1974; D. A. Eckerman, *Pharmacol. Biochem. Behav.* 12, 595, 1980) on the mnemic pathway and on the reduction of the levels of acetylcholine in the hippocampus. The effect on memory and learning can be evaluated in rats using the passive-avoidance test, as described by Essman, *Pharmacol. Res. Commun.* 5, 295, 1973.

The subject of the present invention is, moreover, the use of the present compounds of formula (I) or their pharmaceutically acceptable salts or solvates in the treatment of conditions of neuropathic pain, chronic inflammatory pain and visceral pain. Also provided is a method to treat the aforesaid diseases characterised by administering a pharmaceutically active amount of a compound of formula (I) to a patient in need thereof.

It is hypothesized that the process of learning and memory is implicated in the mechanisms of chronic pain (Flor H., *Prog. Brain Res.,* 129, 313, 2000), and recent evidence supports the hypothesis that chronic inflammatory pain is an acquired maladaptive phenomenon (Arnstein P. M., *J. Neurosci. Nurs.* 29, 179, 1997; Kumazava T., *Neurosci. Res.,* 32, 9, 1998). Cognitive dysfunction has been described in various neuropathic conditions (Kuhajda M. C., *Ann. Behav. Med.,* 20, 31, 1998), and it has recently been observed that nefiracetam, a nootropic agent, alleviates neuropathic pain thanks to its specific effects on neuropathies (Rashid Harunor M.D. *J. Pharmacol. Exp. Ther.,* 303, 226, 2002). It has been shown that the analgesic and/or anti-hyperalgesic effect of nefiracetam expresses itself through stimulation of the nicotinic cholinergic receptors at the spinal and supraspinal level, in so far as said effect is inhibited in a dose-dependent way by mecamylamine, a known antagonist of the nicotinic acetylcholine receptor.

The activity of the compounds of formula (I) can be determined in mice by means of the thermal-hyperalgesia test (paw-withdrawal test) and the mechanical-hyperalgesia test (paw-pressure test) induced by partial ligation of the sciatic nerve or by treatment with streptozotocine, following the protocols described in J. *Pharmacol. Exp. Ther.*, 303, 226, 2002 and in the bibliography cited therein.

When used in the therapeutic treatment of humans and animals, the compounds of formula (I) are normally formulated, in compliance with standard pharmaceutical practice, as a pharmaceutical composition.

Hence, a further subject of the invention is represented by a pharmaceutical composition comprising, as active principle, a compound of formula (I) or one of its pharmaceutically acceptable salts or solvates, together with vectors, diluents and pharmaceutically acceptable excipients suitable for the chosen form of administration.

The compounds of formula (I) can be administered in a standard way in the treatment of the disorders Indicated above, for example via oral, parenteral, rectal, transdermal route or by administration through the mucosa (for example, the sublingual, buccal, or nasal mucosa).

The compounds of formula (I) which are administered orally or via sublingual route or via buccal administration, can be formulated as syrups, tablets, capsules, and lozenges. A formulation in the form of syrup consists generally of a suspension or solution of the compound or of one of its salts in a liquid vector, for example ethanol, glycerine or water with a flavouring or colouring agent. When the composition is in the form of tablets, It is possible to use any pharmaceutical vector used conventionally in the preparation of solid formulations. Examples of said vectors comprise magnesium stereate, starch, lactose and sucrose. When the composition is in the form of capsules, any conventional method of encapsulation is suitable, for example using the vectors mentioned above in a capsule of hard gelatins. When the composition is in the form of capsules made of soft gelatins, it is possible to use any pharmaceutical vector used conventionally in the preparation of dispersions or suspensions, for example aqueous gums, cellulose, silicates or oils, to be incorporated into a shell made of soft gelatine.

Typical parenteral compositions consist of a solution or suspension of the compound of formula (I) In a aqueous or non-aqueous sterile vector, possibly containing an oil acceptable for the parenteral route, for example polyethylene-glycol, polyvinylpyrrolidone, lecithin, peanut oil, or sesame oil.

The typical formulation in suppositories comprises a compound of formula (I), which is active if administered in this way, with a binding and/or lubricating agent, for example polymeric glycols, gelatine, cocoa butter, or other low-melting waxes or vegetable fats.

Typical transdermal formulations comprise a conventional aqueous or non-aqueous vector, for example cream, ointment; lotion or paste, or can be in the form of medicated plasters, patches or membranes.

Preferably, the composition is in a unit-dose form, for example tablets or capsules, so that the patient can take a single dose.

Oxyracetam is a compound used in the treatment of senile dementia and of pathological conditions correlated thereto. The compounds of formula (I) can be administered with regimes similar to the ones established for oxyracetam with any appropriate adjustment of the levels of dosage or of the frequency of dosage in relation to the greater activity and to the better pharmacological profile of the compounds of formula (I).

Each dosage unit for oral administration may expediently contain from 0.05 mg/kg to 50 mg/kg, more expediently from 0.1 mg/kg to 25 mg/kg of a compound of formula (I). The active Ingredient can be administered from 1 to 6 times a day. The compounds of formula (I) can be co-administered with other pharmaceutically active compounds, for example in association, concurrently or sequentially, in particular together with other compounds used in the treatment of elderly patients, such as tranquilizers, diuretics, anti-hypertensive drugs, vasodilator drugs, and inotropic agents.

Examples of the present invention are provided in what follows, purely for illustrative and non-limiting purposes.

EXPERIMENTAL PART

Description 1. 3-isobutyl-tetrahydro-pyrrolo[1,2-a] imidazole-2,5-dione

To a solution of DL-leucinamide hydrochloride (1.5 g, 9 mmol) in water (40 ml), adjusted to pH 9.5 with 10% sodium hydroxide, ethyl-4-oxobutanoate (1 g, 7.5 mmol) was added. The mixture was placed in a microwave oven and refluxed for 1 hour. Water was then evaporated under vacuum and the residue was chromatographated over silica gel ($CH_2Cl_2$/ MeOH/$NH_4OH$ 98/2/0.1) to afford 1.1 g of the title compound.

$^1$H-NMR ($CDCl_3$) δ: 6.48 (broad s, 1H); 5.30 (t, 1H); 4.23 (dd, 1H); 2.71-2.39 (m, 3H); 2.20-1.93 (m, 1H); 1.86-1.73 (m, 1H); 1.70-1.42 (m, 2H); 1.05 (d, 3H); 0.96 (d, 3H). MS: EI TSQ 700; source 180 C; 70 V; 200 uA: 196 (M+), 97.

Example 1

1-Phenyl-tetrahydro-1H-pyrrolo[1,2-a]imidazole-2, 5-dione

To a solution of tetrahydro-pyrrolo[1,2-a]imidazole-2,5-dione (1 g, 7.14 mmol; prepared as described in *J. Med. Chem.* 36, 4214-4220, 1994,) in N-methylpyrrolidone (NMP, 12 cc), CuI (0.2 g, 1.05 mmol), $K_2CO_3$ (1 g, 7.14 mmol) and Iodobenzene (5 g, 24.5 mmol) were added under stirring. The suspension was heated in a microwave apparatus (250 Watt) for 45 min. Ethyl acetate was added to the suspension and the solid was filtered. The organic phase was washed with water and the aqueous phase was re-extracted with $CH_2Cl_2$. The organic phases were gathered and dried over $Na_2SO_4$, filtered and concentrated to dryness. The residue was triturated with isopropyl ether. The solid was filtered, triturated with water and filtered to yield 0.18 g of the title compound, mp=185-188° C.

$^1$H-NMR ($CDCl_3$) δ: 7.46-7.37 (m, 4H); 7.28-7.21 (m, 1H); 5.84 (m, 1H); 4.48 (d, 1H); 3.74 (d, 1H); 2.78-2.60 (m, 2H); 2.51-2.38 (m, 1H); 2.08-1.96 (m, 1H). MS: EI TSQ 700; source 180 C; 70 V; 200 uA: 216 (M+), 160, 97.

Example 2

1-o-tolyl-tetrahydro-1H-pyrrolo[1,2-a]imidazole-2,5-dione

To a solution of tetrahydro-pyrrolo[1,2-a]imidazole-2,5-dione (1.3 g, 9.28 mmol, prepared as described in *J. Med. Chem.* 36,4214, 1994) in N-methylpyrrolidone (NMP, 12 cc), CuI (0.5 g, 2.62 mmol), $K_2CO_3$ (1.3 g, 9.28 mmol) and 2-bromotoluene (6 g, 35 mmol) were added under stirring. The suspension was heated in a microwave apparatus (250 Watt) for 1 h. Ethyl acetate was added to the suspension and the solid was filtered. The organic phase was washed with water and the aqueous phase was re-extracted with $CH_2Cl_2$. The organic phases were gathered and dried over $Na_2SO_4$, filtered and concentrated to dryness. The residue was triturated with $Et_2O$. The solid was filtered, and crystallized the first time with iPrOH and then with AcOEt to yield 0.33 g of the title compound, mp=138-139° C.

$^1$H-NMR ($CDCl_3$) δ: 7.35-7.23 (m, 4H); 7.13-7.06 (m, 1H); 5.69 (m br, 1H); 4.45 (d, 1H); 3.78 (d, 1H); 2.68 (ddd, 1H); 2.48 (ddd, 1H); 2.40-2.29 (m, 1H); 2.24 (s, 3H); 1.93 (m br, 1H). MS: EI TSQ 700; source 180 C; 70 V; 200 uA: 230(M+), 143, 118, 97.

Example 3-44

(Table 1). General Procedure for Arylation of tetrahydro-pyrrolo[1,2-a]imidazole-2,5-diones with aryl halides To a solution of tetrahydro-pyrrolo[1,2-a]imidazole-2,5-dione (3.5 mmol; prepared as described in *J. Med. Chem.* 36, 4214-4220, 1994 or in WO-9309120), in N-methylpyrrolidone (NMP 1 ml), CuI (0.19 g, 1 mmol), $K_2CO_3$ (0.5 g, 3.5 mmol) and the appropriate aryl halide (7 mmol) were added under stirring. The suspension was heated in a microwave apparatus (25 Watt) for 20 min. Ethyl acetate (50 ml) and water (5 ml) were added to the suspension and the mixture was stirred for 30' in the presence of celite. The reaction was filtered and the ethyl acetate was washed with a saturated solution of NaCl, dried over $Na_2SO_4$, filtered and concentrated to dryness. The residue was triturated with $Et_2O$ to give the desired compound. Yields vary from 30% to 60%.

Example 45

1-Benzyl-tetrahydro-pyrrolo[1,2-a]imidazole-2,5-dione

A solution of tetrahydro-pyrrolo[1,2-a]imidazole-2,5-dione (0.5 g, 3.5 mmol, prepared as described in *J. Med. Chem.* 36, 4214, 1994), BEMP (2 ml, 7 mmol) and benzylbromide (0.6 ml, 5 mmol) in $CH_3CN$ (20 ml) was refluxed for 1 hour. The reaction mixture was concentrated to dryness; the residue was then re-dissolved in ethyl acetate and washed with a saturated solution of NaCl, dried over $Na_2SO_4$, filtered and evaporated under vacuum. The residue was purified by flash chromatography over silica gel ($CH_2Cl_2$/MeOH/$NH_4OH$ 95/5/0.5) to afford 0.7 g of the title compound as yellow oil.

Yield: 87% $^1$H-NMR ($CDCl_3$) δ: 7.39-7.10 (m, 5H); 5.03 (dd, 1H); 4.71 (d, 1H); 4,29 (d, 1H); 4.28 (d, 1H); 3.59 (d, 1H); 2,57 (ddd, 1H); 2.39-2.125 (m, 2H); 1.92-1.77 (m, 1H). MS: EI TSQ 700; source 180 C; 70 V; 200 uA: 230.13 (M+), 174.09, 139.04, 91.03.

Example 46

1-(4-methylbenzyl)-tetrahydro-pyrrolo[1,2-a]imidazole-Z 5-dione

A solution of tetrahydro-pyrrolo[1,2-a]imidazole-2,5-dione (0.5 g, 3.5 mmol, prepared as described in *J. Med. Chem.* 36, 4214, 1994), BEMP (2 ml, 7 mmol) and 4-methylbenzylbromide (0.95 ml, 5 mmol) in $CH_3CN$ (20 ml) was refluxed for 1 hour. The reaction mixture was concentrated to dryness; the residue was then re-dissolved in ethyl acetate and washed with a saturated solution of NaCl, dried over $Na_2SO_4$, filtered and evaporated under vacuum. The residue was purified by flash chromatography over silica gel ($CH_2Cl_2$/MeOH/$NH_4OH$ 95/5/0.5) to afford 0.8 g of the title compound as yellow oil.

Yield: 93% $^1$H-NMR ($CDCl_3$) δ: 7.29-7.11 (m, 4H); 5.01 (m, 1H); 4.69 (d, 1H); 4.29 (d, 1H); 4.23 (d, 1H); 3.58 (d, 1H); 2.65-2.50 (m, 1H); 2.40-2.24 (m, 2H); 2.33 (s, 3H); 1.93-1.78 (m, 1H). MS: EI TSQ 700; source 180 C; 70 V; 200 uA: 244.13 (M+), 161.05, 105.02

TABLE 1

Structure, chemical name (generated by Bellstein's Autonom), $^1$H NMR, MS and melting point data for compounds prepared according to the general procedure described above.

| Ex. | Structure | Chemical name | Analytical data |
|---|---|---|---|
| 3 | 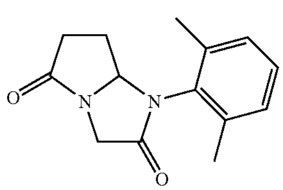 | 1-(2,6-Dimethyl-phenyl)-tetrahydro-pyrrolo[1,2-a]imidazole-2,5-dione | $^1$H-NMR ($CDCl_3$) δ: 7.24-7.10 (m, 3 H); 5.63 (dd, 1 H); 4.48 (d, 1 H); 3.82 (d, 1 H); 2.70 (ddd, 1 H); 2.51 (ddd, 1 H); 2.33-2.18 (m, 1 H); 2.26 (s, 3 H); 2.20 (s, 3 H), 2.06-1.91 (m, 1 H). MS: EI TSQ 700; source 180° C.; 70 V; 200 uA: 244 (M+); 97. |
| 4 | 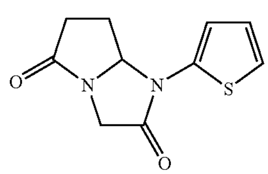 | 1-Thiophen-2-yl-tetrahydro-pyrrolo[1,2-a]imidazole-2,5-dione | $^1$H-NMR ($CDCl_3$) δ: 7.05 (dd, 1H); 6.93 (dd, 1 H); 6.65 (dd, 1 H); 5.67 (m, 1 H); 4.49 (d, 1 H); 3.77 (d, 1 H); 2.88-2.69 (m, 2 H); 2.58-2.45 (m, 1 H); 2.33-2.21 (m, 1 H). MS: EI TSQ 700; source 160° C.; 70 V; 200 uA: 222 (M+); 194; 166; 97. mp: 170-171° C. |

TABLE 1-continued

Structure, chemical name (generated by Bellstein's Autonom), $^1$H NMR, MS and melting point data for compounds prepared according to the general procedure described above.

| Ex. | Structure | Chemical name | Analytical data |
|---|---|---|---|
| 5 | 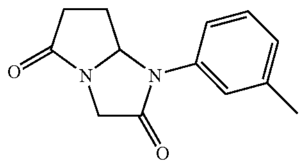 | 1-m-Tolyl-tetrahydro-pyrrolo[1,2-a]imidazole-2,5-dione | $^1$H-NMR (CDCl$_3$) δ: 7.30 (dd, 1 H): 7.24 (dd, 1 H); 7.13 (dd, 1H); 7.07 (dd, 1 H); 5.82 (m, 1 H); 4.46 (d, 1 H); 3.74 (d, 1 H); 2.79-2.57 (m, 2 H); 2.45 (m, 1 H); 2.38 (s, 3 H); 1.08-1.94 (m, 1 H). MS: EI TSQ 700; source 180° C.; 70 V; 200 uA: 230 (M+); 174; 97. mp: 92-93° C. |
| 6 | 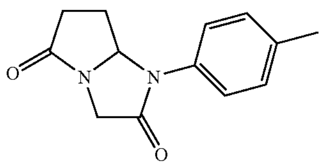 | 1-p-Tolyl-tetrahydro-pyrrolo[1,2-a]imidazole-2,5-dione | $^1$H-NMR (CDCl$_3$) δ: 7.27 (d, 2 H); 7.24 (d, 2 H): 5.79 (m, 1 H); 4.45 (d, 1 H); 3.73 (d, 1 H); 2.72 (ddd, 1 H); 2.70 (m, 1 H); 2.47 (dd, 1 H); 2.38 (s, 3 H); 2.08-1.98 (m, 1 H). MS: EI TSQ 700; source 180° C.; 70 V; 200 uA: 230 (M+); 174; 118. mp: 117-118° C. |
| 7 | 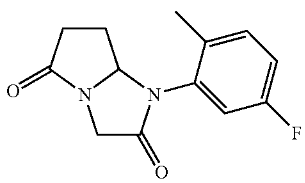 | 1-(5-Fluoro-2-methyl-phenyl)-tetrahydro-pyrrolo[1,2-a]imidazole-2,5-dione | $^1$H-NMR (CDCl$_3$) δ: 7.28 (m, 1 H); 7.02 (ddd, 1 H); 6.85 (dd, 1 H); 5.64 (m br, 1 H); 4.43 (d, 1 H); 3.77 (d, 1 H); 2.70 (dt, 1 H); 2.53-2.31 (m, 2 H); 2.18 (s, 3 H); 1.90 (broad m, 1 H). MS: EI TSQ 700; source 180° C.; 70 V; 200 uA: 248 (M+); 97. mp: 147-148° C. |
| 8 | 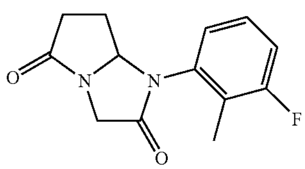 | 1-(3-Fluoro-2-methyl)-phenyl)-tetrahydro-pyrrolo[1,2-a]imidazole-2,5-dione | $^1$H-NMR (CDCl$_3$) δ: 7.23 (ddd, 1 H); 7.07 (dd br, 1 H); 6.92 (d, 1 H); 5.83-5.41 (broad m, 1 H); 4.46 (d, 1 H); 3.78 (d, 1 H); 2.69 (ddd, 1 H); 2.48 (ddd, 1 H); 2.45-2.29 (m, 1 H); 2.14 (d, 3 H); 1.89 (broad m, 1 H). MS: EI TSQ 700; source 180° C.; 70 V; 200 uA: 248 (M+); 136; 109. mp: 135-137° C. |
| 9 | 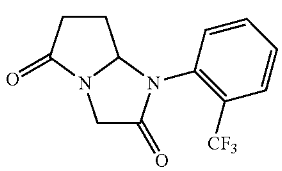 | 1-(2-Trifluoromethyl-phenyl)-tetrahydro-pyrrolo[1,2-a]imidazole-2,5-dione | $^1$H-NMR (CDCl$_3$) δ: 7.81 (d, 1 H); 7.66 (dd, 1 H); 7.54 (broad dd, 1 H); 7.27 (d, 1 H); 5.64 (m, 1 H); 4.42 (broad d, 1 H); 3.72 (d, 1 H); 2.63 (m, 1 H); 2.48 (m, 1 H); 2.28 (m, 1 H); 2.03 (m, 1 H). MS: EI TSQ 700; source 180° C.; 70 V; 200 uA: 284 (M+); 228; 198; |
| 10 | 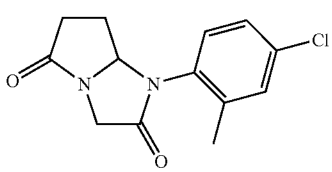 | 1-(4-Chloro-2-methyl-phenyl)-tetrahydro-pyrrolo[1,2-a]imidazole-2,5-dione | $^1$H-NMR (CDCl$_3$) δ: 7.32 (d, 1 H); 7.24 (dd, 1 H); 7.04 (d, 1 H); 5.63 (broad m, 1 H); 4.44 (d, 1 H); 3.77 (d, 1 H); 2.69 (ddd, 1 H); 2.48 (ddd, 1 H); 2.35 (m, 1 H); 2.22 (s, 3 H); 1.92 (m, 1 H). MS: EI TSQ 700; source 180° C.; 70 V; 200 uA: 264 (M+); 97. mp: 122-124° C. |
| 11 | 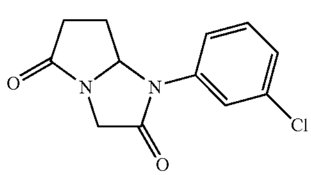 | 1-(3-Chloro-phenyl)-tetrahydro-pyrrolo[1,2-a]imidazole-2,5-dione | $^1$H-NMR (CDCl$_3$) δ: 7.46 (m, 1 H); 7.39-7.28 (m, 2 H); 7.22 (ddd, 1 H); 5.81 (m, 1 H); 7.48 (d, 1 H); 3.73 (d, 1 H); 2.85-2.64 (m, 2 H); 2.46 (m, 1 H); 2.03 (m, 1 H). MS: EI TSQ 700; source 180° C.; 70 V; 200 uA: 250 (M+); 194, 138, 111. mp: 123-125° C. |
| 12 | 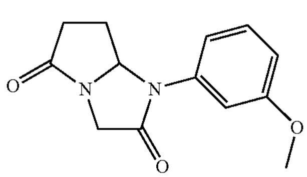 | 1-(3-Methoxy-phenyl)-tetrahydro-pyrrolo[1,2-a]imidazole-2,5-dione | $^1$H-NMR (CDCl$_3$) δ: 7.31 (dd, 1 H); 7.06 (dd, 1 H); 6.91 (dd, 1 H); 6.79 (dd, 1 H); 5.80 (m, 1 H); 4.46 (d, 1 H); 3.82 (s, 3 H); 3.73 (d, 1 H); 2.79-2.61 (m, 2 H); 2.45 (m, 1 H); 2.12-1.96 (m, 1 H). MS: EI TSQ 700; source 180° C.; 70 V; 200 uA: 248 (M+); 190. mp: 94-95° C. |

TABLE 1-continued

Structure, chemical name (generated by Bellstein's Autonom), ¹H NMR, MS and melting point data for compounds prepared according to the general procedure described above.

| Ex. | Structure | Chemical name | Analytical data |
|---|---|---|---|
| 13 | 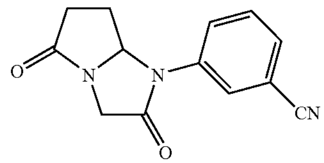 | 1-(3-Cyano-phenyl)-tetrahydro-pyrrolo[1,2-a]imidazole-2,5-dione | $^1$H-NMR (CDCl$_3$) δ: 7.73 (m, 2 H); 7.52 (m, 2 H); 5.81 (m, 1 H); 4.51 (m, 1 H); 3.73 (d, 1 H); 2.64-2.65 (m, 2 H); 2.47 (dd, 1 H); 2.11-1.95 (m, 1 H). MS: EI TSQ 700; source 180° C.; 70 V; 200 uA: 241 (M+); 185, 129. mp: 128-130° C. |
| 14 | 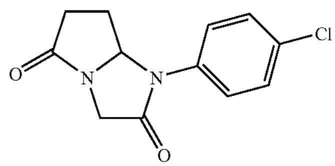 | 1-(4-Chloro-phenyl)-tetrahydro-pyrrolo[1,2-a]imidazole-2,5-dione | $^1$H-NMR (CDCl$_3$) δ: 7.42-7.32 (m, 4 H); 5.80 (m, 1 H); 4.46 (d, 1 H); 3.73 (d, 1 H); 2.79-2.60 (m, 2 H); 2.45 (m, 1 H); 2.09-1.93 (m, 1 H). MS: EI TSQ 700; source 180° C.; 70 V; 200 uA: 250 (M+); 194. mp: 159-160° C. |
| 15 | 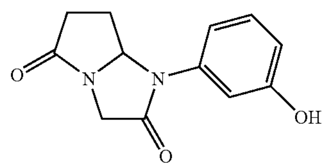 | 1-(3-Hydroxy-phenyl)-tetrahydro-pyrrolo[1,2-a]imidazole-2,5-dione | $^1$H-NMR (CDCl$_3$) δ: 7.16 (dd, 1 H); 6.96 (dd, 1 H); 6.76 (dd, 1 H); 6.69 (dd, 1 H); 5.74 (m, 1 H); 4.38 (d, 1 H); 3.67 (d, 1 H); 2.74-2.55 (m, 2 H); 2.38 (m, 1 H); 2.07-1.90 (m, 1 H). MS: EI TSQ 700; source 180° C.; 70 V; 200 uA: 232 (M+.); 176. mp: 210-211° C. |
| 16 | 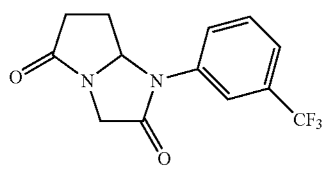 | 1-(3-Trifluoromethyl-phenyl)-tetrahydro-pyrrolo[1,2-a]imidazole-2,5-dione | $^1$H-NMR (CDCl$_3$) δ: 7.68 (d, 1 H); 7.86 (broad s, 1 H); 7.58 (dd, 1 H); 7.50 (d, 1 H); 5.88 (m, 1 H); 4.50 (d, 1 H); 3.76 (d, 1 H); 2.73 (m, 2 H); 2.46 (m, 1 H); 2.04 (m, 1 H). MS: EI TSQ 700; source 180° C.; 70 V; 200 uA 264 (M+); 228; 172; mp: 124-125 C. |
| 17 | 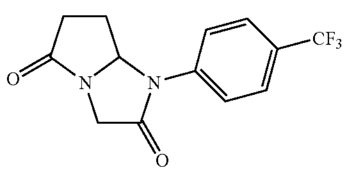 | 1-(4-Trifluoromethyl-phenyl)-tetrahydro-pyrrolo[1,2-a]imidazole-2,5-dione | $^1$H-NMR (CDCl$_3$) δ: 7.68 (d, 2 H); 7.57 (d, 2 H); 5.88 (m, 1 H); 4.50 (d, 1 H); 3.75 (d, 1 H); 2.82-2.67 (m, 2 H); 2.48 (m, 1 H); 2.12-1.96 (m, 1 H). MS: EI TSQ 700; source 180° C.; 70 V; 200 uA: 284 (M+); 228; 172; 145. |
| 18 | 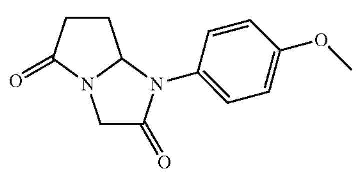 | 1-(4-Methoxy-phenyl)-tetrahydro-pyrrolo[1,2-a]imidazole-2,5-dione | $^1$H-NMR (CDCl$_3$) δ: 7.28 (d, 2 H): 6.95 (d, 2 H); 5.74 (m, 1 H); 4.44 (d, 1 H); 3.81 (s, 3 H); 3.73 (d, 1 H); 2.79.2.39 (m, 3 H); 2.08-1.94 (m, 1 H). MS: EI TSQ 700; source 180° C.; 70 V; 200 uA: 246 (M+): 190; 134. mp: 210-211° C. |
| 19 | 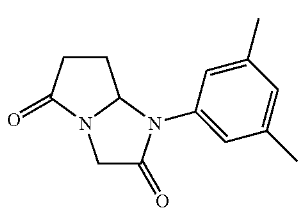 | 1-(3,5-Dimethyl-phenyl)-tetrahydro-pyrrolo[1,2-a]imidazole-2,5-dione | $^1$H-NMR (CDCl$_3$) δ: 6.98 (s, 2 H); 6.89 (s, 1 H); 5.79 (m, 1 H) 4.45 (d, 1 H); 3.72 (d, 1 H); 2.77-2.53 (m, 2 H); 2.44 (m, 1 H); 2.33 (s, 6 H); 2.00 (m, 1 H). MS: EI TSQ 700; source 180° C.; 70 V; 200 uA: 244 (M+); 188; 97. mp: 103-104° C. |
| 20 | 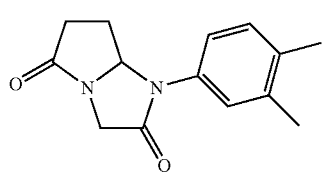 | 1-(3,4-Dimethyl-phenyl)-tetrahydro-pyrrolo[1,2-a]imidazole-2,5-dione | $^1$H-NMR (CDCl$_3$) δ: 7.18 (d, 1 H); 7.16 (d, 1 H); 7.04 (dd, 1 H); 5.77 (dd, 1 H); 4.44 (d, 1 H); 3.72 (d, 1 H); 2.78-2.52 (m, 2 H); 2.44 (m, 1 H); 2.28 (s, 3 H); 2.25 (s, 3 H); 2.08-1.93 (m, 1 H). MS: ZQ, ESI POS, spray 3.25 KV; source 30 V; Probe 250° C.: 245 (MH+). mp: 142-143° C. |

TABLE 1-continued

Structure, chemical name (generated by Bellstein's Autonom), $^1$H NMR, MS and melting point data for compounds prepared according to the general procedure described above.

| Ex. | Structure | Chemical name | Analytical data |
|---|---|---|---|
| 21 | 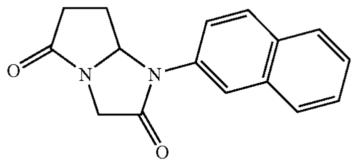 | 1-Naphthalen-2-yl-tetrahydro-pyrrolo[1,2-a]imidazole-2,5-dione | $^1$H-NMR (CDCl$_3$) δ: 7.90 (d, 1 H); 7.83 (m, 2 H); 7.76 (d, 1 H); 7.81 (dd, 1 H); 7.55-7.45 (m, 2 H); 5.97 (m, 1 H); 4.53 (d, 1 H); 2.80 (d, 1 H); 2.86-2.66 (m, 2 H); 2.47 (m, 1 H); 2.15-1.99 (m, 1 H). MS: ZQ, ESI POS, spray 3.25 KV; source 30 V; probe 250° C.: 267 (MH+). mp: 175-176° C. |
| 22 | 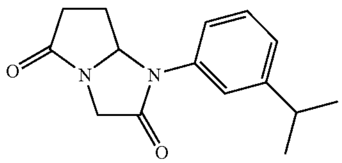 | 1-(3-Isopropyl-phenyl)-tetrahydro-pyrrolo[1,2-a]imidazole-2,5-dione | $^1$H-NMR (CDCl$_3$) δ: 7.33 (dd, 1 H); 7.27 (m, 1 H); 7.17 (d br, 1 H); 7.12 (broad d, 1 H); 5.83 (m, 1 H); 4.46 (d, 1 H); 3.74 (d, 1 H); 2.92 (m, 1 H); 2.80-2.57 (m, 2 H); 2.46 (m, 1 H); 2.04 (m, 1 H); 1.26 (d, 6 H). MS: ZQ, ESI POS, spray 3.25 KV; source 30 V; probe 250° C.: 259 (MH+). mp: 81-82° C. |
| 23 | 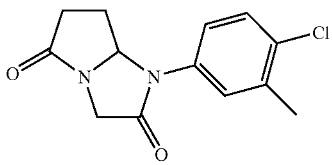 | 1-(4-Chloro-3-methyl-phenyl)-tetrahydro-pyrrolo[1,2-a]imidazole-2,5-dione | $^1$H-NMR (CDCl$_3$) δ: 7.37 (d, 1 H); 7.33 (d, 1 H); 7.12 (dd, 1 H); 5.79 (m, 1 H); 4.46 (d, 1 H); 3.72 (d, 1 H); 2.79-2.58 (m, 2 H); 2.52-2.37 (m, 1 H); 2.40 (s, 3 H); 2.09-1.93 (m, 1 H). MS: ZQ, ESI POS, spray 3.25 KV; source 30 V; probe 250° C.: 265 (MH+). mp: 138-139° C. |
| 24 | 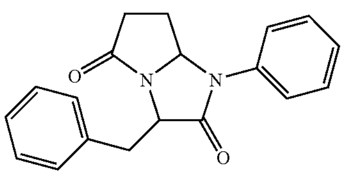 | 3-Benzyl-1-phenyl-tetrahydro-pyrrolo[1,2-a]imidazole-2,5,-dione | $^1$H-NMR (CDCl$_3$) δ: 7.34 (dd, 2 H); 7.28-7.17 (m, 6 H); 7.03 (d, 2 H); 4.77 (m, 1 H); 4.59 (dd, 1 H); 3.32 (dd, 1 H); 3.16 (dd, 1 H); 2.64 (ddd, 1 H); 2.46-2.27 (m, 2 H); 1.81 (m, 1 H). MS: AQA, ESI Pos, 3.5 KV; source 30 V; probe 250° C.: 307 (MH+). mp: 134-136° C. |
| 25 | 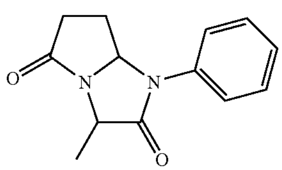 | 3-Methyl-1-phenyl-tetrahydro-pyrrolo[1,2-a]imidazole-2,5,-dione | $^1$H-NMR (CDCl$_3$) δ: 7.42 (m, 4 H); 7.23 (m, 1 H); 5.83 (m, 1 H); 4.54 (q, 1 H), 2.78-2.59 (m, 2 H); 2.45 (m, 1 H); 2.10-1.93 (m, 1 H); 1.47 (d, 3 H). MS: AQA, ESI Pos, 3.5 KV; source 30 V; probe 250° C.: 231 (MH+). mp: 137-138° C. |
| 26 | 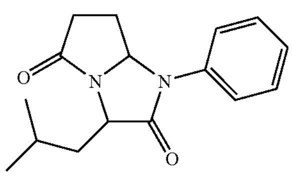 | 3-Isobutyl-1-phenyl-tetrahydro-pyrrolo[1,2-a]imidazole-2,5,-dione | $^1$H-NMR (CDCl$_3$) δ: 7.41 (m, 4 H); 7.22 (m, 1 H); 5.81 (m, 1 H); 4.50 (dd, 1 H); 2.78-2.58 (m, 2 H); 2.45 (m, 1 H); 2.07-1.65 (m, 3 H); 1.54 (m, 1 H); 1.08 (d, 3 H); 0.98 (d, 3 H). MS: AQA, ESI Pos, 3.5 KV; source 30 V; probe 250° C.: 273 (MH+). mp: 101-102° C. |
| 27 | 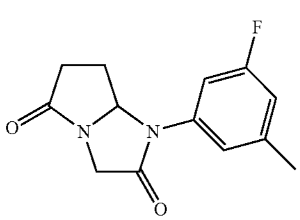 | 1-(3-Fluoro-5-methyl-phenyl)-tetrahydro-pyrrolo[1,2-a]imidazole-2,5-dione | $^1$H-NMR (CDCl$_3$) δ: 6.99 (m, 2 H); 6.77 (d br, 1 H); 5.78 (m, 1 H); 4.46 (d, 1 H); 3.73 (d, 1 H); 2.84-2.63 (m, 2 H); 2.45 (m, 1 H); 2.37 (s, 3 H); 2.11-1.94 (m, 1 H). MS: AQA, ESI Pos, 3.5 KV; source 30 V; probe 250° C.: 249 (MH+). mp: 111-113° C. |
| 28 | 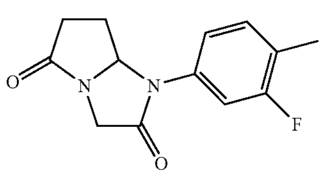 | 1-(3-Fluoro-4-methyl-phenyl)-tetrahydro-pyrrolo[1,2-a]imidazole-2,5-dione | $^1$H-NMR (CDCl$_3$) δ: 7.32-7.18 (m, 2 H); 7.05 (dd br, 1 H); 5.78 (m, 1 H); 4.46 (d, 1 H); 3.73 (d, 1 H); 2.78-2.63 (m, 2 H); 2.50-2.41 (m, 1 H); 2.56 (s, 3 H); 2.11-1.94 (m, 1 H). MS: ZQ, ESI POS, spray 3.25 KV; source 30 V; probe 250° C.: 248 (MH+), 192, 97. mp: 136-137° C. |

TABLE 1-continued

Structure, chemical name (generated by Bellstein's Autonom), $^1$H NMR, MS and melting point data for compounds prepared according to the general procedure described above.

| Ex. | Structure | Chemical name | Analytical data |
|---|---|---|---|
| 29 | 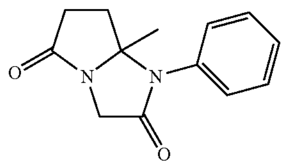 | 7a-Methyl-1-phenyl-tetrahydro-pyrrolo[1,2-a]imidazole-2,5-dione | $^1$H-NMR (CDCl$_3$) δ: 7.52-7.20 (m, 5 H); 4.44 (d, 1 H); 3.78 (d, 1 H); 2.83-2.68 (m, 1 H); 2.56-2.42 (m, 2 H); 2.18-2.30 (m, 1 H), 1.63 (s, 3 H). MS: ZQ, ESI POS, spray 3.25 KV; source 30 V; probe 250° C.: 230 (MH+). mp: 154-155° C. |
| 30 | 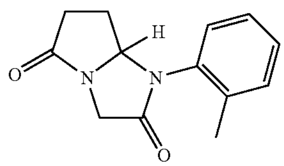 | (S)-1-o-Tolyl-tetrahydro-pyrrolo[1,2-a]imidazole-2,5-dione | $^1$H-NMR (CDCl$_3$) δ; 7.35-7.23 (m, 4 H); 7.13-7.06 (m, 1 H); 5.69 (m br, 1 H); 4.45 (d, 1 H); 3.78 (d, 1 H); 2.68 (ddd, 1 H); 2.48 (ddd, 1 H); 2.40-2.29 (m, 1 H); 2.24 (s, 3 H); 1.93 (m br, 1 H). MS: AQA, ESI Pos, 3.5 KV; source 30 V; probe 250° C.: 230 (M+), 143, 118, 97. [α]$_D$ = −51.39 (c = 0.4, MeOH). |
| 31 | 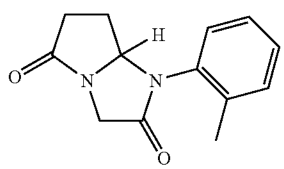 | (R)-1-o-Tolyl-tetrahydro-pyrrolo[1,2-a]imidazole-2,5-dione | $^1$H-NMR (CDCl$_3$) δ; 7.35-7.23 (m, 4 H); 7.13-7.06 (m, 1 H): 5.69 (m br, 1 H); 4.45 (d, 1 H); 3.78 (d, 1 H); 2.68 (ddd, 1 H); 2.48 (ddd, 1 H); 2.40-2.29 (m, 1 H); 2.24 (s, 3 H); 1.93 (m br, 1 H). MS: AQA, ESI Pos, 3.5 KV; source 30 V; probe 250° C.: 230 (M+), 143, 118, 97. [α] = +52.24 (c = 0.4, MeOH). |
| 32 | 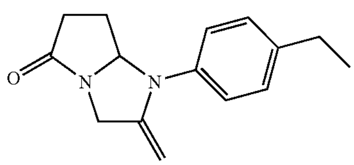 | 1-(4-Ethyl-phenyl)-tetrahydro-pyrrolo[1,2-a]-imidazole-2,5-dione | $^1$H-NMR (CDCl$_3$) δ: 7.29 (d, 2 H); 7.25 (d, 2 H); 5.80 (m, 1 H); 4.45 (d, 1 H); 3.74 (d, 1 H); 2.78-2.56 (m, 2 H); 2.65 (q, 2 H); 2.51-2.38 (m, 1 H); MS: AQA, ESI Pos, 3.5 KV; source 30 V; proble 250° C.: 245.1 (M+). mp: 98-99° C. |
| 33 | 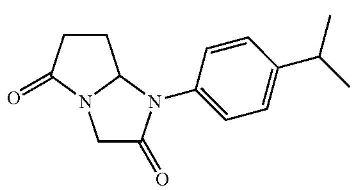 | 1-(4-Isopropyl-phenyl)-tetrahydro-pyrrolo[1,2-a]imidazole-2,5-dione | $^1$H-NMR (CDCl$_3$) δ: 7.32-7.25 (m, 4 H); 5.58 (m, 1 H); 4.46 (d, 1 H); 3.74 (d, 1 H); 2.91 (m, 1 H); 2.78-2.57 (m, 2 H); 2.51-2.40 (m, 1 H); 2.15-1.96 (m, 1 H); 1.24 (d, 6 H). MS: AQA, ESI Pos, 3.5 KV; source 30 V; probe 250° C.: 259.1 (MH+). mp: 124-125° C. |
| 34 | 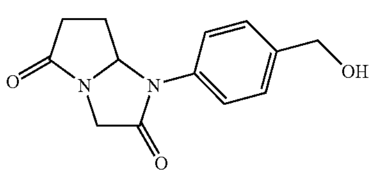 | 1-(4-Hydroxymethyl-phenyl)-tetrahydro-pyrrolo[1,2-a]imidazole-2,5-dione | $^1$H-NMR (CDCl$_3$) δ: 7.41 (m, 4 H); 5.83 (m, 1 H); 4.70 (s, 2 H); 4.47 (d, 1 H); 3.74 (d, 1 H); 2.79-2.59 (m, 2 H); 2.52-237 (m, 1 H); 2.10-1.93 (m, 1 H); 1.72 (s br, 1 H). MS: AQA, ESI Pos, 3.5 KV; source 30 V; probe 250° C.: 247.1 (MH+). mp: 159-161° C. |
| 35 | 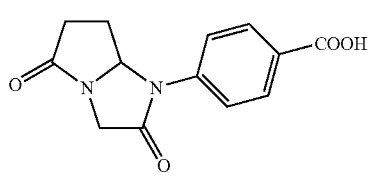 | 4-(2,5-Dioxo-hexahydro-pyrrolo[1,2-a]imidazole-1-yl)-benzoic acid | $^1$H-NMR (CDCl$_3$) δ: 8.06 (d, 2 H); 7.47 (d, 2 H); 5.85 (m, 1 H); 4.43 (d, 1 H); 3.71 (d, 1 H); 2.77-2.61 (m, 2 H); 2.5-2.36 (m, 1 H); 2.05-1.91 (m, 1 H). MS: AQA, ESI Pos, 3.5 KV; source 30 V; probe 250° C.: 261.0 (MH+). mp: 252-253° C. |
| 36 | 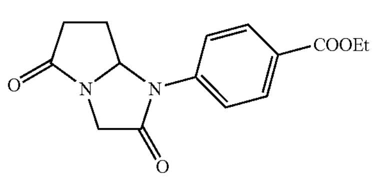 | 4-(2,5-Dioxo-hexahydro-pyrrolo[1,2-a]imidazole-1-yl)-benzoic acid ethyl ester | $^1$H-NMR (CDCl$_3$) δ: 8.10 (d, 2 H); 7.52 (d, 2 H); 5.88 (m, 1 H); 4.50 (d, 1 H); 4.38 (q, 2 H); 3.75 (d, 1 H); 2.82-2.66 (m, 2 H); 2.56-2.38 (m, 1 H); 2.12-1.94 (m, 1 H); 1.39 (t, 3 H). MS: AQA, ESI Pos, 3.5 KV; source 30 V; probe 250° C.: 289.4 (MH+), 218.4. mp: 158-159° C. |

TABLE 1-continued

Structure, chemical name (generated by Bellstein's Autonom), $^1$H NMR, MS and melting point data for compounds prepared according to the general procedure described above.

| Ex. | Structure | Chemical name | Analytical data |
|---|---|---|---|
| 37 | 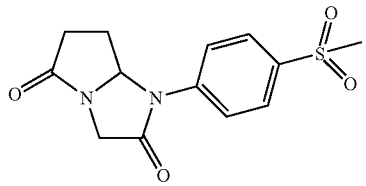 | 1-(4-Methanesulfonyl-phenyl)-tetrahydro-pyrrolo[1,2-a]imidazole-2,5-dione | $^1$H-NMR (CDCl$_3$) δ: 7.98 (d, 2 H); 7.65 (d, 2 H); 5.90 (m, 1 H); 4.52 (d, 1 H); 3.77 (d, 1 H); 3.05 (s, 3 H); 2.84-2.68 (m, 2 H); 2.57-2.42 (m, 1 H); 2.11-1.93 (m, 1 H). MS: AQA, ESI Pos, 3.5 KV; source 30 V; probe 250° C.: 295.1 (MH+) 312.1 (MH + NH3+). mp: 143-145° C. |
| 38 | 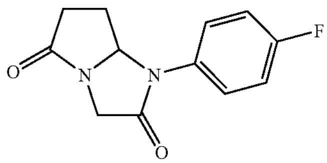 | 1-(4-Fluoro-phenyl)-tetrahydro-pyrrolo[1,2-a]imidazole-2,5-dione | $^1$H-NMR (CDCl$_3$) δ: 7.37 (m, 2 H); 7.12 (dd, 2 H); 5.78 (m, 1 H), 4.47 (d, 1 H); 3.74 (d, 1 H); 2.80-2.56 (m, 2 H); 2.46 (m, 1 H); 2.08-1.93 (m, 1 H). MS: AQA, ESI Pos, 3.5 KV; source 30 V; probe 250° C.: 235.1 (MH+). mp: 158-159° C. |
| 39 | 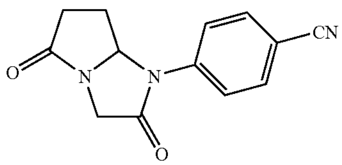 | 1-(4-Cyano-phenyl)-tetrahydro-pyrrolo[1,2-a]imidazole-2,5-dione | $^1$H-NMR (CDCl$_3$) δ: 7.72 (d, 2 H); 7.60 (d, 2 H); 5.87 (m, 1 H); 4.52 (d, 1 H); 3.76 (d, 1 H); 2.84-2.68 (m, 2 H); 2.57-2.43 (m, 1 H); 2.14-1.94 (m, 1 H). MS: AQA, ESI Pos, 3.5 KV; source 30 V; probe 250° C.: 242.1 (MH+). mp: 175-176° C. |
| 40 | 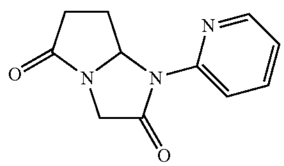 | 1-Pyridin-2-yl-tetrahydro-pyrrolo[1,2-a]imidazole-2,5-dione | $^1$H-NMR (CDCl$_3$) δ: 3.34 (ddd, 1 H); 8.20 (ddd, 1 H); 7.75 (ddd, 1 H); 7.11 (ddd, 1 H); 6.04 (dd, 1 H); 4.52 (d, 1 H); 3.79 (d, 1 H); 3.09-2.97 (m, 1 H); 2.78-2.64 (m, 1 H); 2.41 (ddd, 1 H); 2.15-2.00 (m, 1 H). MS: AQA, ESI Pos, 3.5 KV; source 30 V; probe 250° C.: 218.4 (MH+). mp: 139-140° C. |
| 41 | 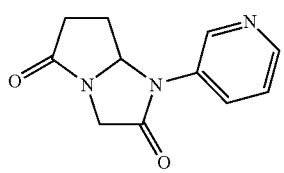 | 1-Pyridin-3-yl-tetrahydro-pyrrolo[1,2-a]imidazole-2,5-dione | $^1$H-NMR (CDCl$_3$) δ: 8.55 (m, 2 H); 8.04 (d, 1 H); 7.39 (m, 1 H); 5.88 (m, 1 H); 4.50 (d, 1 H); 3.75 (d, 1 H); 2.84-2.67 (m, 2 H); 2.58-2.40 (m, 1 H); 2.14-1.95 (m, 1 H). MS: AQA, ESI Pos, 3.5 KV; source 30 V; probe 250° C.: 218.4 (MH+) mp: 180-182° C. |
| 42 | 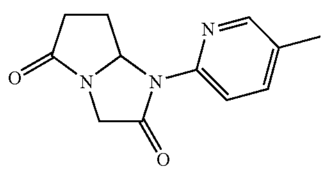 | 1-(5-Methylpyridin-2-yl)-tetrahydropyrrolo[1,2-a]imidazole-2,5-dione | $^1$H-NMR (CDCl$_3$) δ: 8.15 (d, 1 H); 8.07 (d, 1 H); 7.55 (dd, 1 H); 6.02 (dd, 1 H); 4.49 (d, 1 H); 3.77 (d, 1 H); 3.05-2.94 (m, 1 H);; 2.77-2.62 (m, 1 H); 2.40 (ddd, 1 H); 2.31 (s, 3 H); 2.12-1.97 (m, 1 H). MS: AQA, ESI Pos, 3.5 KV; source 30 V; probe 250° C.: 232.1 (MH+). mp: 158-159° C. |
| 43 | 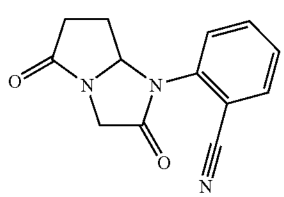 | 1-(2-Cyano-phenyl)-tetrahydro-pyrrolo[1,2-a]imidazole-2,5-dione | $^1$H-NMR (CDCl$_3$) δ: 7.78 (d, 1 H); 7.70 (dd, 1 H); 7.48 (dd, 1 H); 7.38 (d, 1 H); 5.95 (m, 1 H); 4.50 (d, 1 H); 3.81 (d, 1 H); 2.85-2.64 (m, 1 H); 2.58-2.41 (m, 2 H); 2.08-1.93 (m, 1 H). MS: AQA, ESI Pos, 3.5 KV; source 30 V; probe 250° C.: 242.1 (MH+). mp: 94-95° C. |
| 44 | 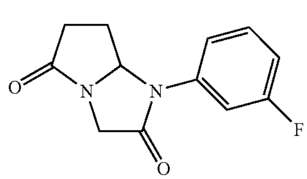 | 1-(3-Fluoro-phenyl)-tetrahydro-pyrrolo[1,2-a]imidazole-2,5-dione | $^1$H-NMR (CDCl$_3$) δ: 7.38 (ddd, 1 H); 7.29 (ddd, 1 H); 7.15 (ddd, 1 H); 6.95 (dddd, 1 H); 5.81 (m, 1 H); 4.49 (d, 1 H); 3.75 (d, 1 H); 2.85-2.65 (m, 2 H); 2.53-2.40 (m, 1 H); 2.13-1.97 (m, 1 H). MS: AQA, ESI Pos, 3.5 KV; source 30 V; probe 250° C.: 235.1 (MH+). mp: 145-149° C. |

Pharmacological Methods

Chronic Constriction Injury Model

A peripheral mononeuropathy was produced in adult rats by placing loosely constrictive ligatures around the common sciatic nerve according to the method described by Bennett & Xie (*Pain* 1968, 33, 87-107).

Rats were anesthetized with chloral hydrate. The common sciatic nerve was exposed at the level of the middle of the thigh by blunt dissection through biceps femoris. Proximal to sciatica's trifurcation, about 1 cm of the nerve was freed of adhering tissue and four ligatures (3/0 silk tread) were tied loosely around it with about 1 mm spacing. The length of the nerve thus affected was 1 cm long. Great care was taken to tie the ligatures such that the diameter of the nerve was seen to be just barely constricted when viewed with 40× magnification. The left paw was untouched.

Paw Pressure Test

The nociceptive threshold in the rat was determined with an analgesimeter (Ugo Basile, Varese, Italy), according to the method described by Leighton et al. (*Br. J. Pharmacol.* 1988, 93, 553-560). Rats scoring below 40 g or over 75 g during the test before drug administration (25%) were rejected. An arbitrary cut-off value of 250 g was adopted.

All experiment were performed on rats submitted to paw-pressure test 14 days after the operation since at this time a significantly reduction of the pain threshold of the injured paw (dx) was observed.

Gabapentin (30 μg i.c.v.), levetiracetam (300 μg i.c.v.), dimiracetam (100 μg i.c.v.), Example 1 (10 μg i.c.v.), Example 2 (10 μg i.c.v.), Example 5 (3 μg i.c.v.), Example 6 (3 μg i.c.v.), Example 13 (30 μg i.c.v.) and Example 22 (30 μg i.c.v.) of the present invention showed an antihyperalgic effect when compared with saline or vehicle treated group. All compounds did not modify pain threshold in controlateral, non operated, paw. It should be noted that all compounds elicited their antihyperalgic effect without changing animals' gross behavior and spontaneous motility in comparison with saline/vehicle treated rats. Furthermore no modification of motor coordination was revealed by the rat rota-rod test (Vaught J. et al. *Neuropharmacology* 1985, 24, 211-216).

EFFECT OF COMPOUNDS OF THE INVENTION AND REFERENCE COMPOUNDS (i.c.v.) IN A RAT MODEL OF MONONEUROPATHY dx EVALUATED IN THE PAW-PRESSURE TEST

| TREATMENT | (i.c.v.) | PAW | Paw pressure in rats (g) Before Treatment | After Treatment |
|---|---|---|---|---|
| SALINE | | dx | 24.3 ± 2.9 | 23.7 ± 2.5 |
| VEHICLE | | dx | 26.5 ± 3.5 | 22.9 ± 3.6 |
| GABAPENTIN | 30 μg | dx | 24.5 ± 4.7 | 46.3 ± 4.2* |
| LEVETIRACETAM | 300 μg | dx | 24.0 ± 3.9 | 37.3 ± 4.6^ |
| DIMIRACETAM | 100 μg | dx | 25.1 ± 2.4 | 42.8 ± 2.5* |
| EXAMPLE 1 | 10 μg | dx | 26.0 ± 2.2 | 36.3 ± 5.1^ |
| EXAMPLE 2 | 10 μg | dx | 23.5 ± 4.0 | 42.2 ± 3.9* |
| EXAMPLE 5 | 3 μg | dx | 27.7 ± 2.8 | 39.3 ± 4.5^ |
| EXAMPLE 6 | 3 μg | dx | 26.7 ± 3.6 | 46.1 ± 5.0^ |
| EXAMPLE 13 | 30 μg | dx | 28.5 ± 2.9 | 55.4 ± 4.7* |
| EXAMPLE 22 | 30 μg | dx | 25.4 ± 2.7 | 48.5 ± 4.6* |

Each value represents the mean of at least 8 rats (two separate experiments).
All compounds were administered 30-45 min before test.
^ P < 0.05;
* P < 0.01

The invention claimed is:

1. A process for the preparation of compounds of the general formula (I)

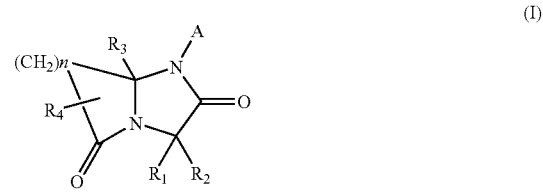

wherein:
A is selected from the group consisting of carbocyclic aromatic groups, heterocyclic aromatic groups, and aryl$C_{1-4}$alkyl;
$R_1$ is selected from the group consisting of:
hydrogen,
aryl$C_{1-7}$alkyl, optionally substituted on the aryl moiety with one or more groups chosen among hydroxy, $C_{1-4}$alkoxy, halogen, halo$C_{1-4}$alkyl;
heterocyclyl$C_{1-7}$alkyl, optionally substituted on the heterocyclyl moiety with one or more groups chosen among $C_{1-4}$alkyl and hydroxy; and
$C_{1-7}$ alkyl, optionally interrupted by an oxygen or sulphur atom or optionally substituted at any position by one or more groups chosen among hydroxy, thio, amino, carboxyl, aminocarbonyl, guanidinyl;
$R_2$ is selected from the group consisting of hydrogen, $C_{1-4}$alkyl, aryl$C_{1-4}$alkyl and phenyl;
or else $R_1$ and $R_2$, taken together, form a saturated carbocyclic ring containing from 3 to 8 carbon atoms;
$R_3$ is selected from the group consisting of hydrogen, $C_{1-4}$alkyl, aryl$C_{1-4}$alkyl, $CONH_2$ and $COOR_5$ in which $R_5$ is selected from the group consisting of hydrogen and $C_{1-4}$alkyl;
$R_4$ is selected from the group consisting of hydrogen, $C_{1-4}$alkyl, aryl, aryl$C_{1-4}$alkyl and heterocyclyl;
n is 2, 3 or 4;
in the form of a racemic mixture or in the form of enantiomers, and pharmaceutically acceptable salts thereof, comprising the following stages:
i) reacting an aminoacid of formula (IV) or of one of its activated derivatives

with a compound of formula (V)

to obtain a compound of formula (VI):

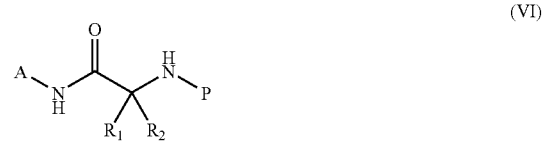

in which $R_1$, $R_2$ and A are as defined above, and P is H or a suitable protective group;

ii) reacting the compound of formula (VI) obtained in stage i) with a compound of formula (VII)

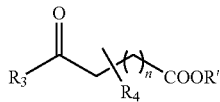

(VII)

to obtain a compound of formula (VIII)

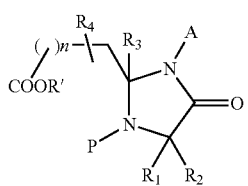

(VIII)

in which A, $R_1$, $R_2$, $R_3$, $R_4$ and n are as defined above, P is defined as above, and R' is an alkyl group;

iii) optionally removing the protective group P by means of hydrogenolysis of the compound of formula (VIII) obtained from stage ii), to obtain the corresponding compound (VIII), in which P is H; and iv) cyclizing of the compound of formula (VIII), in which P is H coming from stage ii) or from stage iii), to obtain the desired compound of formula (I).

2. The process according to claim 1, wherein R' is selected from the group consisting of methyl and tert-butyl, and P is selected from the group consisting of H, benzyl and benzyloxycarbonyl.

3. The process according to claim 1, wherein in said stage iv), the cyclization reaction is carried out by heating the compound (VIII) in the absence of solvent at 120° C. and in vacuum conditions, or else by reflux-heating the compound (VIII) in xylene for a time comprised between 4 hours and 3 days.

4. The process according to claim 1, wherein said stage ii) is conducted by reflux-heating the compounds of formula (VI) and (VII) in a protic solvent for a time period between 2 and 24 hours, optionally in the presence of a base.

5. The process according to claim 1, wherein the reaction in stage i) is conducted between the acidic chloride of the compound (IV) and the compound (V) in the presence of an inorganic or organic base in a suitable aprotic solvent at a temperature of between −70° C. and 50° C.

6. The process according to claim 1, wherein the reaction of stage i) is conducted by reacting together the compound (IV) and the compound (V) in the presence of a suitable condensating agent, in an aprotic solvent at a temperature of between −70° C. and 50° C.

7. The process according to claim 5, wherein said temperature is between −10° C. and 20° C.

8. The process according to claim 6, wherein said temperature is between −10° C. and 20° C.

* * * * *